(12) United States Patent
Sorebo et al.

(10) Patent No.: US 6,716,203 B2
(45) Date of Patent: Apr. 6, 2004

(54) INDIVIDUAL ABSORBENT ARTICLES WRAPPED IN A QUIET AND SOFT PACKAGE

(75) Inventors: Heather A. Sorebo, Appleton, WI (US); Wendy Benhke, Neenah, WI (US); Julie Bednarz, Neenah, WI (US); David R. Wagner, Neenah, WI (US); Robert J. Koenig, Roswell, GA (US); Kimberly A. Stanford, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/022,808

(22) Filed: Dec. 18, 2001

(65) Prior Publication Data

US 2003/0120241 A1 Jun. 26, 2003

(51) Int. Cl.⁷ .............................................. A61F 13/15
(52) U.S. Cl. .............................. 604/385.02; 604/385.13
(58) Field of Search ...................... 654/385.02, 385.13, 654/385.01, 385.04, 387, 390, 389; 206/440, 438

(56) References Cited

U.S. PATENT DOCUMENTS

| | | | |
|---|---|---|---|
| 3,193,181 A | * | 7/1965 | Konjevich et al. ........ 229/87.15 |
| 3,674,029 A | * | 7/1972 | Bates et al. ................. 604/366 |
| 3,849,241 A | | 11/1974 | Buntin et al. |
| 3,973,567 A | * | 8/1976 | Srinivasan et al. .... 604/385.05 |
| 4,556,146 A | * | 12/1985 | Swanson et al. ............ 206/440 |
| 4,627,849 A | | 12/1986 | Walton et al. |
| 4,857,066 A | * | 8/1989 | Allison .................. 604/385.13 |
| 4,881,644 A | | 11/1989 | Norquest et al. |
| 5,088,993 A | * | 2/1992 | Gaur ...................... 604/385.02 |
| 5,181,610 A | * | 1/1993 | Quick et al. ................. 206/447 |
| 5,389,181 A | | 2/1995 | Vukos et al. |
| 5,413,568 A | | 5/1995 | Roach et al. |
| 5,569,228 A | * | 10/1996 | Byrd et al. ............. 604/385.02 |
| 5,843,057 A | | 12/1998 | McCormack |
| 5,954,201 A | | 9/1999 | Finch et al. |
| 6,036,679 A | | 3/2000 | Balzar et al. |
| 6,063,065 A | * | 5/2000 | Costa ..................... 604/385.02 |
| 6,074,376 A | * | 6/2000 | Mills .......................... 604/390 |
| 6,276,032 B1 | | 8/2001 | Nortman et al. |
| 6,293,932 B1 | | 9/2001 | Balzar et al. |
| 6,299,607 B1 | * | 10/2001 | Osborn et al. ......... 604/385.02 |
| 6,500,160 B2 | * | 12/2002 | Mizutani et al. ....... 604/385.02 |
| 2002/0040213 A1 | * | 4/2002 | Tweddell, III et al. .. 604/385.01 |
| 2003/0102238 A1 | * | 6/2003 | White et al. ................ 206/438 |

FOREIGN PATENT DOCUMENTS

| | | |
|---|---|---|
| EP | 0597446 B1 | 4/1998 |
| EP | 1022125 A1 | 7/2000 |
| WO | WO 9619349 | 6/1996 |
| WO | WO 9802610 | 1/1998 |
| WO | WO 9829239 | 7/1998 |
| WO | WO 9912734 | 3/1999 |
| WO | WO 0020208 | 4/2000 |
| WO | WO 0130564 | 5/2001 |

\* cited by examiner

*Primary Examiner*—Weilun Lo
*Assistant Examiner*—Jacqueline F Stephens
(74) *Attorney, Agent, or Firm*—Dority & Manning, P.A.

(57) ABSTRACT

An individually wrapped feminine care absorbent article package includes an absorbent article contained within a pouch having an openable flap. The pouch is made from a wrapper material having an inner film layer and at least one fibrous material outer layer having a tactile cloth-like softness as compared to the film layer.

23 Claims, 3 Drawing Sheets

INDIVIDUAL ABSORBENT ARTICLES WRAPPED IN A QUIET AND SOFT PACKAGE

BACKGROUND OF THE INVENTION

The present invention relates to individually wrapped absorbent articles such as catamenial pads. More specifically, the invention relates to improved packaging of such products.

Absorbent feminine care articles such as sanitary napkins, panty liners, and other types of catamenial devices are used to absorb menses and other body fluids. These absorbent products are used during a women's menstrual cycle and are primarily disposable. In addition, disposable absorbent articles are also used between menstrual cycles for light incontinence purposes. Since many of these articles are carried in a woman's purse or pocket prior to use, it is advantageous to individually wrap each article to keep it clean and sanitary. By individually packaging each absorbent article, the manufacturer can be assured that the article will not become contaminated by the contents of the user's purse, pocket, etc.

Conventionally, the article wrapper consists of one or more layers of a thin sheet or film of thermoplastic material, such as polyethylene, which is folded around the absorbent article and then sealed by the use of heat and/or pressure, ultrasonics, or an adhesive to form a package or pouch. The package is designed to be opened by breaking or tearing the material at or adjacent a seal in order to subsequently remove the absorbent article. Conventional packages are also typically designed so that a soiled article can be wrapped up in the opened package for later disposal.

Most women value their personal privacy and prefer not to advertise to others that they are carrying or using feminine care products. For some individuals, the "public" use of such products can be an anxious and often traumatic experience. Unfortunately, conventional wrapping materials and package designs may only exacerbate this problem. Conventional films used in many absorbent wrappers are inherently "loud" when manipulated. The material "crinkles" when shaken or moved and is particularly loud when the package is opened and the absorbent article is removed, particularly if the article is adhered to the inside of the wrapper. Often, the exercise of locating the article in a purse or carry bag is announced to those in relatively close proximity by the sound of the package once it is located and removed. The same situation applies to opening the package. Thus, the consumer's ability to discreetly and quietly store and open the absorbent article is hampered by the packaging materials.

Thus, a package for individually wrapped articles, particularly feminine care articles, that can be quietly stored, carried, and opened is desirable to avoid embarrassing and anxious moments for consumers. The present invention addresses this need.

SUMMARY

Objects and advantages of the invention will be set forth in part in the following description, or may be obvious from the description, or may be learned through practice of the invention.

The present invention relates to a unique wrapper or package for individually wrapped absorbent articles, particularly feminine pads, liners, tampons, and the like. The package includes a wrapper material configured into a pouch, wherein the absorbent article is stored in the pouch. The wrapper material includes a film layer that may be fluid impervious. The film layer may be vapor permeable. Various film materials are well known and widely used in the art for this purpose. The wrapper material also includes at least one fibrous material layer having a tactile cloth-like softness as compared to the film layer. The material layers may be laminated to each other.

The invention is not limited to any particular pouch configuration. It is believed that the wrapper material according to the invention will offer distinct advantages in any conventional pouch configuration as compared to the same pouch configuration made solely from a film layer or layers. In one particularly beneficial pouch embodiment, the wrapper material is folded at a first fold axis such that a first end is folded towards the opposite second end and bonded along aligned longitudinal sides to define the pouch. The fibrous material is outwardly disposed and thus defines the outer surfaces of the pouch. The second end of the wrapper material is folded at a second fold axis back over onto a front surface of the pouch to define a flap. This flap may have various lengths. For example, the flap may extend so as to be generally adjacent the first fold axis, or even extend beyond the fold axis. On the other hand, the flap may extend onto the front surface of the pouch just enough to overlap the first end of the wrapper material. The flap is subsequently adhered or attached relative to the front side of the pouch. For example, the longitudinal sides of the flap may be bonded with the sides of the pouch such that three layers of the wrapper material are bonded together along the common bond seams. The flap sides are, however, bonded to the fibrous layer of the wrapper material along at least a portion thereof. Any conventional process may be utilized to bond the respective flap sides and pouch sides including, for example, a thermal embossing process.

The applicants have found that with use of the unique film/fibrous laminate wrapper material according to the invention, unique "quieter" seams are possible as compared to conventional film pouches, particularly the flap seams. With conventional film pouches, the inherent "loudness" is a result of the characteristics of the film material and is particularly enhanced along the seams where film material is bonded to film material and thus seams are thicker and stiffer. The process of breaking or separating the flap seams to open the pouches is a relatively noisy event. The noise associated with the seams and the opening process is reduced with pouches according to the present invention. The side seams of the pouches are more pliant and thus less noisy, and the flap seams are separated to open the pouches with far less noise.

The present invention also encompasses a method related to the unique absorbent article pouches and wrapping system. As discussed in the Background section, the storage and use of feminine care products can be an anxious and at times traumatic experience for certain consumers. The present invention provides a method for reducing such consumer anxiety related to carrying, use and disposal of feminine care absorbent articles. The method includes providing the feminine care absorbent articles to consumers in individually wrapped discreet and quiet packages that do not draw unnecessary attention to the consumer. The method involves choosing a combination of wrapping materials for the packages specifically to minimize noise associated with carrying, manipulating, and opening the packages while still providing barrier protection for the absorbent articles carried within the packages. The materials may also be chosen with respect to color, surface pattern, etc., so as to provide an unremarkable and discreet appearance, as compared to certain trends in the industry wherein brand name recognition and product identification are emphasized by providing the articles to consumers in bright and bold colored individual film packages. Such packages cannot help but draw attention to the consumer. The wrapping material according to the present invention would provide a benefit even to these packages.

The invention will be described in greater detail below through reference to the attached figures and particular embodiments of the invention.

DETAILED DESCRIPTION

Figure 1:
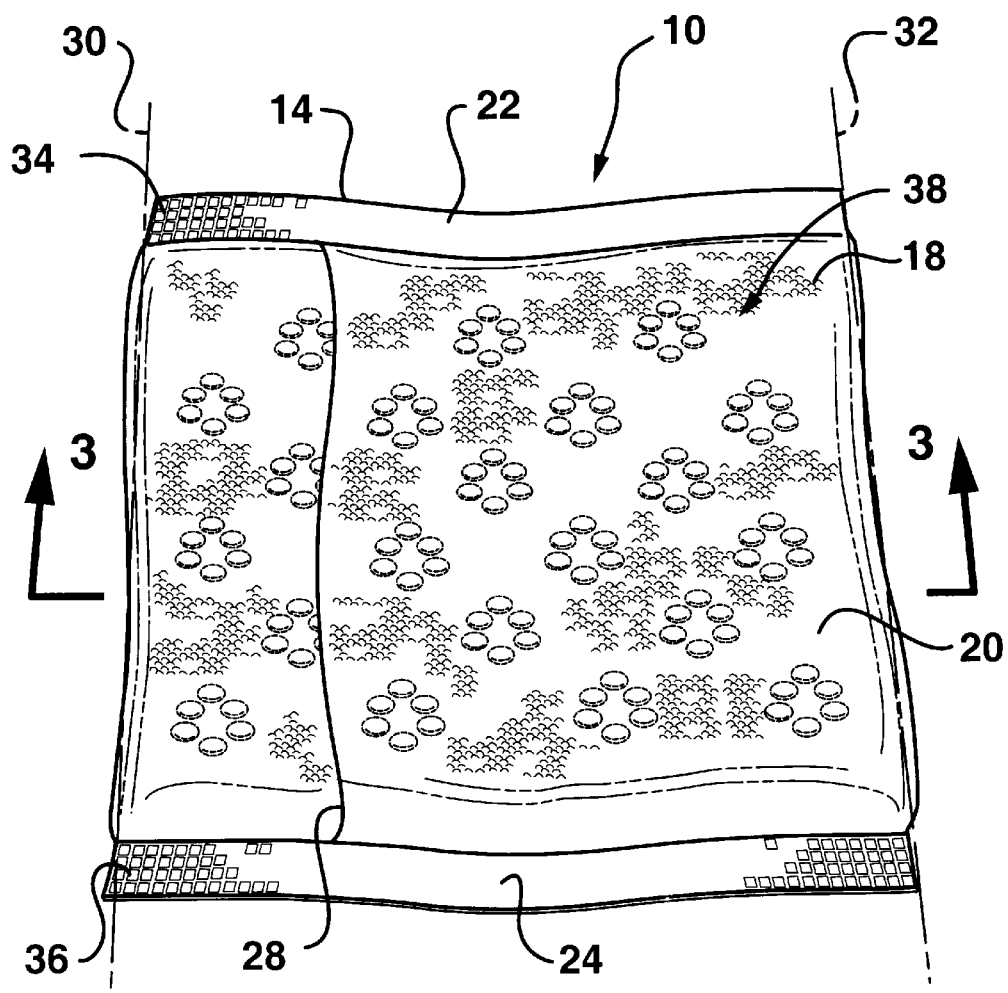
FIG. 1 is a perspective view of an individually wrapped absorbent article package according to the invention.

Reference will now be made in detail to one or more embodiments of the invention, at least one example of which is shown in the drawings. The embodiments are provided by way of explanation of the invention, and not meant as a limitation of the invention. For example, features illustrated or described as part of one embodiment may be used with another embodiment to yield still a different embodiment. It is intended that the present invention include these and other modifications and variations as come within the scope and spirit of the invention.

Figure 2:
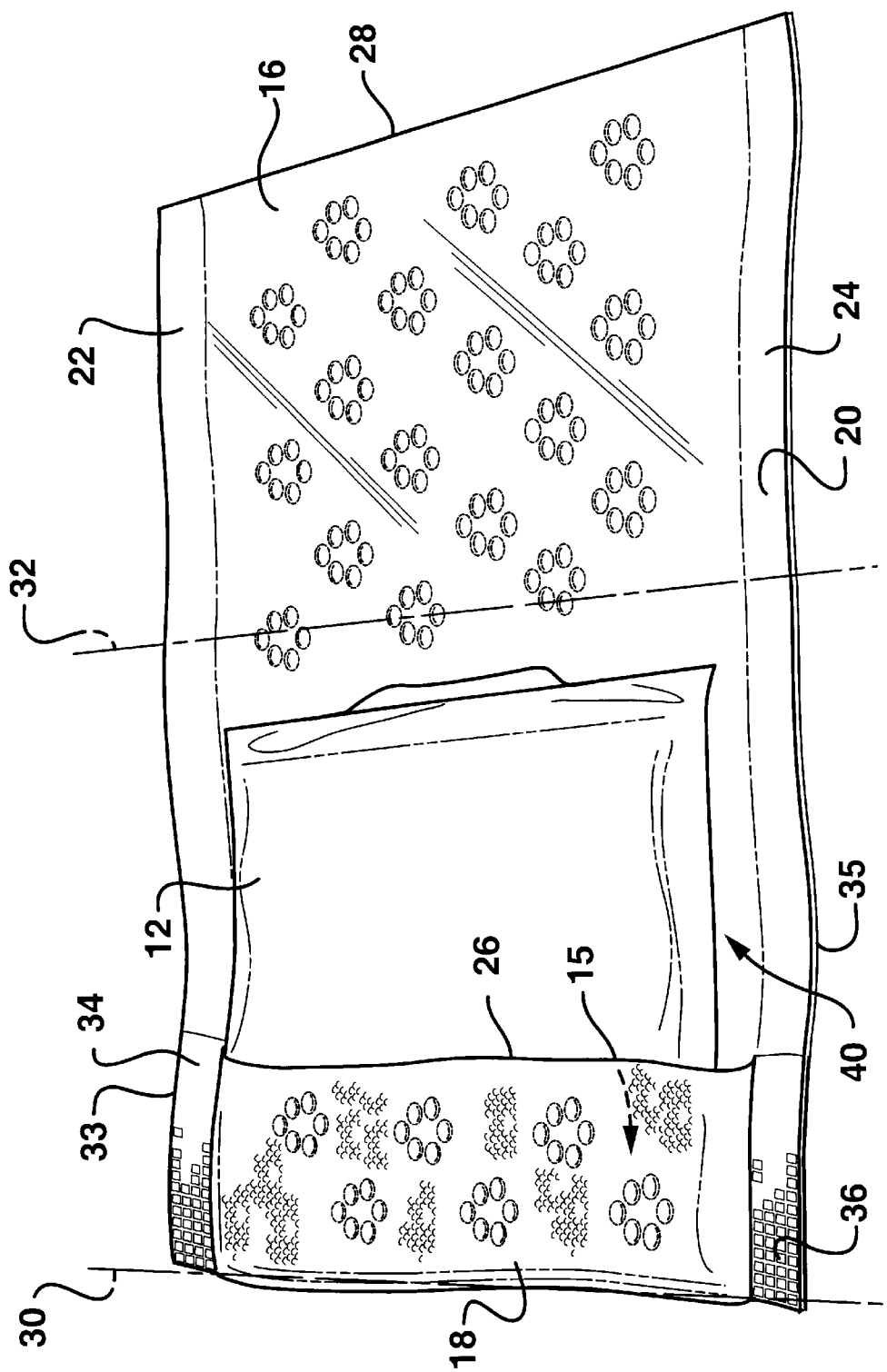
FIG. 2 is a perspective view of the package of FIG. 1 shown in its opened state.
Figure 3:
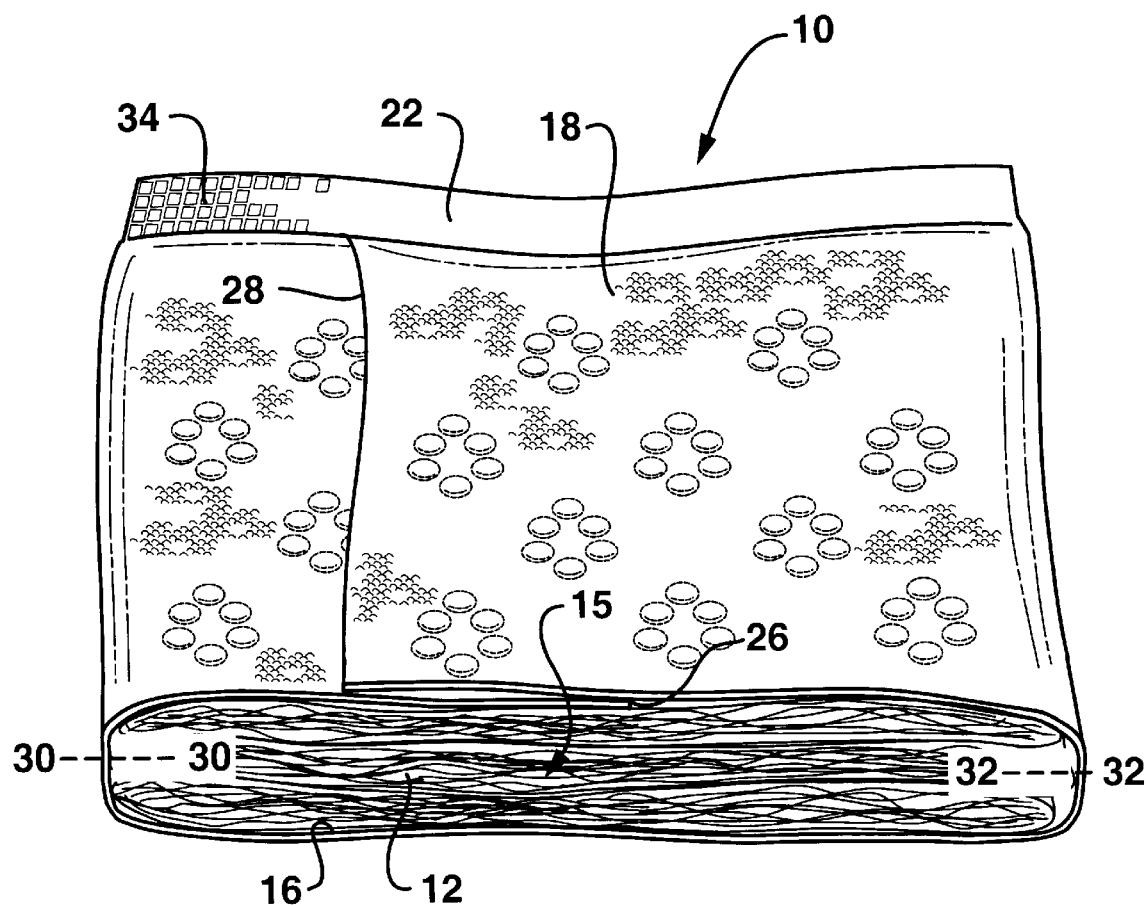
FIG. 3 is a cross-sectional view taken along the lines indicated in FIG. 1.

Referring to the figures, an embodiment of an individually wrapped absorbent article package 10 is generally illustrated. An absorbent article 12 is carried in the package 10, as shown in FIG. 2. The invention is not limited to any particular type of absorbent article. For example, the absorbent article 12, may be a catamenial device such as a sanitary napkin, a panty liner, a labial pad, an incontinence pad, or any other type of absorbent article which can be used to absorb menstrual fluid, urine, body fluid, body exudate, etc. A detailed description of such absorbent articles is not necessary for purposes of the present invention. For purposes of describing the invention only, the absorbent article 12 is shown and referred to herein as a sanitary pad or napkin. The absorbent article 12 may be folded in any desired pattern to fit in the package 10. In the illustrated embodiment, the absorbent article 12 is in a tri-fold pattern, as seen in FIG. 3.

The package 10 includes an elongate piece of wrapper material, generally 14, folded and bonded into a pouch configuration. For example, the wrapper material 14 may be an elongated rectangular piece having a first end 26, an opposite second end 28, and generally parallel longitudinal sides 33 and 35 extending between the ends 26 and 28.

The invention is not limited to any particular type of pouch configuration. Various pouch configurations are known and used in the art for individually packaging feminine care absorbent articles and any such configuration may be used in a package according to the invention. The unique features of the present wrapper material 14 will provide a benefit to any pouch configuration. In the illustrated embodiment, the pouch 15 is similar to the pouch configuration used for Kotex® Ultrathin pads from Kimberly-Clark Corporation.

Referring to FIG. 2, it can be seen that the wrapper material is essentially folded around the absorbent article 12 such that the pouch 15 is formed around the article. The wrapper material 14 is first folded at a first fold axis 30 such that the first end 26 is folded towards but spaced from the second end 28, as can be seen particularly in FIGS. 2 and 3. The distance between the first end 26 and second end 28 may vary depending on the desired length of a resulting flap 20, as described below. The aligned longitudinal sides of the wrapper material 14 define sides 34 and 36 of the pouch 15. The second end 28 of the wrapper material is then folded at a second fold axis 32 so as to extend back over the first end 26 and thus defines the flap 20 that closes off the pouch 15, as particularly seen in FIG. 1. The flap 20 has longitudinal sides 24 and 22 that align with the material sides 33 and 35 and pouch sides 34 and 36. The sides of the package 10 are then bonded in a conventional manner, for example with a heat/pressure embossing roll. The flap sides 22 and 24 are bonded to the material sides 33 and 35 and pouch sides 34 and 36 in a single pass operation. It may be the case that the first end 26 of the wrapper material 14 extends essentially to the second fold axis 32 and, thus, the flap sides 22 and 24 would be bonded along their entire length to pouch sides 34 and 36.

Referring to FIGS. 1 and 3, it can be seen that the edge of the second end 28 extends across the front surface of the pouch 15. It may be desired to adhere all or a portion of this edge to the pouch surface. However, in a desirable embodiment of the package according to the invention, this edge is left un-adhered to the pouch between its bonded sides 22 and 24.

The wrapper material 14 according to the invention may be a laminate material including a first film layer 16 laminated to a second fibrous material layer 18. The film layer 16 includes one or more layers of any conventional film material that is liquid impermeable, but vapor-pervious. The film layer 16 may have any desired color and surface pattern. It may be desired that the film layer 16 have a nondescript color and pattern, such as a neutral color.

The formation of films useful with the present invention is well known to those of ordinary skill in the art and need not be discussed herein in detail. One type of film that may be used is a nonporous, continuous film that, because of its molecular structure, is capable of forming a vapor-pervious barrier. Among the various polymeric films which fall into this category include films made from poly(vinyl alcohol), polyvinyl acetate, ethylene vinyl alcohol, polyurethane, ethylene methyl acrylate, and ethylene methyl acrylic acid to make them breathable. If desired, it is also possible to add fillers to the film such as, for example, calcium carbonate and titanium dioxide, to increase opacity, decrease cost, and create a breathable film if the filled film is subsequently stretched. If the film layer is not sufficiently thin, then it may be necessary to further thin the film by stretching it in an apparatus such as a machine direction orienter (MDO) unit. An MDO has a plurality of stretching rollers which progressively stretch and thin the film in the machine direction (direction of travel of the film through the machine).

Another type of film which may be useful is a microporous film. These films have a number of interconnecting voids or holes which provide pathways for the transportation of water molecules from one surface to another. The passageways are sufficiently small so that only vapors and not fluids can pass through them.

As seen particularly in FIG. 2, the wrapper material 14 is oriented so that the film layer 16 is disposed on the inside of the pouch 15 and thus defines an inner major surface 40.

The wrapper material 14 includes a fibrous material layer 18 that forms an outer major surface 38 of the pouch 15. As used herein, the term "fiber" or "fibrous" refers to elongated individual natural or synthetic strands (as compared to a continuous film layer). Synthetic fibers are formed by passing a polymer through a forming orifice such as a die. Unless noted otherwise, the terms "fibers" or "fibrous" include discontinuous strands having a definite length and continuous strands of material, such as filaments.

The fibrous layer 18 may comprise any one or combination of non-woven or woven materials and is intended to give the pouch a soft and cloth-like tactile feel and to dampen and reduce noise associated with storing, carrying, and opening the pouches 15. Non-woven materials may be preferred from a manufacturing standpoint. However, woven materials, including any manner of synthetic or natural cloth, are within the scope and spirit of the invention.

As used herein the term "nonwoven" material means a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

The fibrous material layer 18 may comprise a non-woven meltblown web. Meltblown fibers are formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al. Generally speaking, meltblown fibers may be microfibers that may be continuous or discontinuous, are generally smaller than 10 microns in diameter, and are generally tacky when deposited onto a collecting surface.

The fibrous material layer 18 may comprise a non-woven spunbond web. Spunbonded fibers are small diameter substantially continuous fibers that are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. Nos. 4,340,563 to Appel, et al. 3,692,618 to Dorschner, et al., 3,802,817 to Matsuki et al., 3,338,992 to Kinney, 3,341,394 to Kinney, 3,502,763 to Hartman, 3,502,538 to Levy, 3,542,615 to Dobo, et al., and 5,382,400 to Pike, et al. Spunbond fibers are generally not tacky when they are deposited onto a collecting surface. Spunbond fibers can sometimes have diameters less than about 40 microns, and are often between about 5 to about 20 microns.

The fibrous material layer 18 may comprise a spunbond/meltblown/spunbond, or SMS, material. A typical SMS material is described in U.S. Pat. No. 4,041,203 to Brock et al. Other SMS products and processes are described for example in U.S. Pat. Nos. 5,464,688 to Timmons et al.; 5,169,706 to Collier et al.; and 4,766,029 to Brock et al.

Generally, an SMS material will consist of a meltblown web sandwiched between two exterior spunbond webs. Such SMS laminates have been available commercially for years from Kimberly-Clark Corporation under marks such as Spunguard® and Evolution®. The spunbonded layers on the SMS laminates provide durability and the internal meltblown layer provides porosity and additional cloth-like feel.

Suitable non-woven webs for use as the fibrous material layer 18 may also be made from bonded carded webs and airlaid webs. Bonded carded webs are made from staple fibers which are sent through a combing or carding unit, which separates or breaks apart and aligns the staple fibers to form a nonwoven web. Once the web is formed, it then is bonded by one or more of several known bonding methods.

Airlaying is another well known process by which fibrous webs can be formed. In the airlaying process, bundles of small fibers having typical lengths ranging from about 6 to about 19 millimeters are separated and entrained in an air supply and then deposited onto a forming screen, usually with the assistance of a vacuum supply. The randomly deposited fibers then can be bonded to one another using known bonding techniques.

The film layer 16 and fibrous material layer 18 are laminated together by any lamination technique known to those skilled in the art. Suitable lamination means include, but are not limited to, adhesives, ultrasonic bonding and thermomechanical bonding as through the use of heated calendering rolls. Such calendering rolls will often include a patterned roll and a smooth anvil roll, though both rolls may be patterned or smooth and one, both or none of the rolls may be heated. The figures illustrate an aesthetic pattern defined in the laminated wrapper material 14.

Referring to FIG. 2 in particular, it can be seen that once the absorbent article 12 is placed on the inner major surface 40 of the wrapper material 14, the material is folded at the first axis 30 and then at the second axis 32 to define the pouch 15 and flap 20. The sides of the pouch and flap are then bonded or sealed together. These seals or bonds can be formed by heat, heat and pressure, pressure, adhesive, ultrasonic bonding, or other types of bonding techniques know to those skilled in the art. The seals can be made to be a "permanent" seal, which means that the wrapper material adjacent to the seal will tear or break before the sealed layers separate. Alternately, the seals may be "frangible" seals, which means that the sealed layers will separate or pull apart. In a desirable embodiment of the package 10, the seal between the flap sides 24 and 22 and the pouch sides 34 and 36 is a frangible seal formed by simultaneously sealing the pouch sides and flap sides in a single sealing operation with a heated/pressure embossing roll. It has been found that, compared to sealing purely film sides, a greater variance in the sealing temperature may used. The temperature of the embossing roll may be maintained between about 245 degrees Fahrenheit and about 285 degrees Fahrenheit. This temperature range is significantly greater than the range for bonding strictly film layers. Thus, the addition of the fibrous material also provides for greater process flexibility. Above about 285 degrees, the nonwoven layer and film layer tend to separate or delaminate upon opening the pouches. The roll cylinder pressure may be adjusted accordingly to obtain the desired bond characteristics.

In the embodiment illustrated, the consumer opens the pouch by inserting a finger between the flap 20 and front surface of the pouch 15 and then pulling the flap away from the pouch or sliding the finger side-ways to break the sealed sides of the flap. The second end 28 of the wrapper material is preferably not adhered to the front surface of the pouch and it is thus relatively easy for the consumer to insert a finger between the flap and pouch. The noise that is typically associated with the opening procedure is significantly reduced by the seams wherein the film layer side of the flap 20 is sealed to the fibrous layer side of the pouch front surface.

Having described certain specific embodiments of the present invention, a series of sample pouches with a pad inside and without a pad inside were made and tested to further illustrate the present invention. The results of these tests, and the test procedures used, are set forth below.

Test Procedures

Sample pouches of individually wrapped feminine pads according to the invention were made and tested against commercially available products.

The sample pouches were formed from a film/spunbond laminate material available from Kimberly-Clark Corp. and known as HBSTL ("highly breathable stretch thermal laminate"). The HBSTL material includes a polypropylene spunbond material thermally attached to a stretched breathable film. This material is described in greater detail in U.S. Pat. No. 6,276,032. The material is laminated with a patterned calender roll to provide the pattern shown in the figures with an overall bond area of between about 15% to about 20%. The pouches were configured essentially as illustrated in the present figures, which is the pouch configuration of the Kotex® Ultrathin Pouches from Kimberly-Clark Corp. with the exception that the front flap between the sealed sides was not attached or adhered to the front of the pouch as it is with the Kotex®) Ultrathin product.

The pouches were tested against two commercially available products: the Kotex® Ultrathin pouch (all film) and the Always® Ultrathin pouch from Proctor and Gamble Company.

Test One

Twenty-five persons were randomly selected. The pouches were coded and each person was provided one type of each pouch without a product inside (the pouches were empty). Each person was instructed to separately crunch the pouches and to note which pouch (code) was quieter. Each person was then provided one type of each pouch with product inside and asked to conduct the same crunch test. The results of the tests are provided below:

TABLE 1

Results of pouch crunch test

|  | Nonwoven Pouch without Product was Quieter | Nonwoven Pouch with Product was Quieter |
|---|---|---|
| Nonwoven Pouch with Kotex ® Ultrathin | 25 | 21 |
| Kotex ® Ultrathin in commercial pouch | 0 | 1 |
| Always ® Ultrathin in commercial pouch | 0 | 3 |

The nonwoven pouch according to the invention without product was found by all of the participants to be the quietest pouch. The nonwoven pouch with product was found by 21 of 25 of the participants as the quietest pouch.

Test 2

10 samples of each type of pouch identified above with product inside were tested with an electronic noise monitor having a 3-light LED display (Gerry® Baby Monitor Model 611 Listed: 3075 from A Huffy Company in Thorton, Colo. 80241). The monitor was placed on a table one foot from the pouch samples to be tested. The monitor speaker with LED display was placed 20 feet away in a different room with the door between the rooms closed. The 30 pouches were randomly assigned numbers from 1 to 30. One person was assigned to open pouches at the table, and another person was assigned to record the LED read outs at the speaker. Pouch 1 was selected by the person at the table and the number of the pouch was verbally given over the monitor to the person in the other room documenting the LED read outs. With both elbows on the table and hands held about 6 inches off the table and about 12 inches from the monitor, the person at the table opened the pouch. The person at the speaker recorded the number of lit LED lights during the opening sequence. The procedure was repeated for pouches 2 through 30. The results of the test are recorded below:

TABLE 2

Monitor Test Results

| Kotex ® Ultrathin Pouch | Always ® Ultrathin Pouch | Kotex ® Ultrathin Nonwoven Pouch |
|---|---|---|
| 3 | 3 | 1 |
| 3 | 3 | 1 |
| 3 | 3 | 0 |
| 3 | 3 | 1 |
| 3 | 3 | 1 |
| 3 | 3 | 3 |
| 3 | 3 | 1 |
| 3 | 3 | 1 |
| 3 | 3 | 1 |
| 3 | 3 | 1 |

The commercial products (Kotex® Ultrathin and Always® Ultrathin) generated the maximum three-light display for each opening sequence. Of the 10 pouches configured in accordance with the present invention, 1 pouch generated no lights, 8 pouches generated 1 light, and 1 pouch generated 3 lights.

It is intended that the present invention include variations and modifications to the embodiments described herein as come within the scope and spirit the invention as set forth in the appended claims.

What is claimed is:

1. An individually wrapped feminine care absorbent article package, comprising:
   an absorbent article;
   a wrapper material configured into a pouch, said absorbent article disposed within said pouch;
   said wrapper material comprising a film layer and at least one fibrous material layer having a tactile cloth-like softness as compared to said film layer, said layers laminated together, said fibrous material outwardly disposed so as to define outer surfaces of said pouch;
   said wrapper material defining a flap for said pouch, said flap having at least a portion thereof bonded to an outer surface portion of said pouch, wherein said film layer on said flap is bonded to said fibrous material layer on said pouch by only a thermal embossing process; and
   wherein said flap bonded portion is bonded to a front surface of said pouch such that to open said pouch, a consumer pulls said flap to separate said flap bonded portion from said pouch.

2. The package as in claim 1, wherein said absorbent article is one of a sanitary pad, panty liner, incontinence pad, and tampon.

3. The package as in claim 1, wherein said wrapper material is folded at a first fold axis such that a first end of said wrapper material is folded towards a second opposite end to define a portion of said pouch, said wrapper material folded at a second fold axis such that said second end is folded towards said first fold axis and over said first end to define said flap, aligned longitudinal sides of said pouch and flap being bonded together.

4. The package as in claim 3, wherein said flap is unbonded relative to a front side of said pouch between said sides of said flap.

5. The package as in claim 1, wherein said film layer is fluid-impervious.

6. The package as in claim 5, wherein said film layer is vapor permeable.

7. The package as in claim 1, wherein said fibrous material is a woven material.

8. The package as in claim 1, wherein said fibrous material is a non-woven material.

9. The package as in claim 8, wherein said non-woven material is a spunbond material.

10. The package as in claim 8, wherein said non-woven material is a spunbond-meltblown-spunbond material.

11. A method for alleviating consumer anxiety resulting from carrying and use of feminine care absorbent articles, comprising:

providing the feminine care absorbent articles to consumers in individually wrapped packages;

choosing a combination of wrapping materials for the packages specifically to minimize noise associated with carrying, manipulating, opening, and disposing of the packages while still providing barrier protection for the absorbent articles carried within the package; and forming the package from a film material layer for providing the barrier protection and from at least one fibrous material layer for dampening and reducing noise, wherein at least a portion of said film material layer is bonded to at least a portion of said fibrous material layer by a thermal embossing process.

12. The method as in claim 11, further comprising providing the consumers with a way to identify the package by touch.

13. The method as in claim 12, wherein the wrapping materials are also selected to have an outwardly soft and cloth-like tactile feel.

14. The method as in claim 11, further comprising providing the package substantially free of product identifying indicia.

15. The method as in claim 11, further comprising providing the package substantially free of brand-name indicia.

16. The method as in claim 11, comprising forming the package from a film material for providing the barrier protection and from at least one fibrous material for dampening and reducing noise.

17. The method as in claim 16, wherein the fibrous material is selected so as to have a soft and cloth-like tactile feel.

18. The method as in claim 16, wherein the fibrous material is selected from a nonwoven material.

19. A wrapping system for absorbent articles configured for minimizing noise associated with carrying, manipulating, and opening packaging for the absorbent articles, comprising:

a wrapper material comprising a film layer and at least one fibrous material layer having a tactile cloth-like softness as compared to said film layer, said layers laminated to each other;

said wrapper material having opposite longitudinal sides between first and second ends;

said wrapper material folded at a first fold axis such that said fibrous material is outwardly disposed, and said wrapper material bonded along aligned said longitudinal sides to define a pouch having bonded sides and a size for carrying an individual absorbent article therein, said first end of said wrapper material folded at a second fold axis back over onto a front surface of said pouch to define a flap;

said flap having opposite sides thermally bonded with said pouch sides, wherein said film layer on said flap is bonded to said fibrous material layer on said pouch; and wherein to open said pouch, a consumer pulls said flap to separate said flap sides from said pouch sides; and wherein said flap sides are bonded to said pouch sides in a thermal embossing process.

20. The system as in claim 19, wherein said fibrous material is a non-woven material.

21. The system as in claim 19, wherein said flap is unbonded to a front side of said pouch between said bonded sides thereof.

22. The system as in claim 19, wherein said film layer is fluid-impervious.

23. The system as in claim 19, wherein said fibrous material is a woven material.

* * * * *

UNITED STATES PATENT AND TRADEMARK OFFICE
CERTIFICATE OF CORRECTION

PATENT NO.     : 6,716,203 B2
DATED          : April 6, 2004
INVENTOR(S)    : Heather Sorebo et al.

It is certified that error appears in the above-identified patent and that said Letters Patent is hereby corrected as shown below:

<u>Title page,</u>
Item [75], Inventor, "Wendy Benhke" should read -- Wendy Behnke --

Signed and Sealed this

Nineteenth Day of July, 2005

JON W. DUDAS
*Director of the United States Patent and Trademark Office*